United States Patent
Lederer et al.

(10) Patent No.: US 7,880,977 B2
(45) Date of Patent: Feb. 1, 2011

(54) ROD LENS TO BE FITTED IN ENDOSCOPES

(75) Inventors: Frank Lederer, Tuttlingen (DE); Frank Fuerst, Tuttlingen (DE); Matthias Huber, Emmingen-Liptingen (DE); Juergen Rudischhauser, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 756 days.

(21) Appl. No.: 11/693,852

(22) Filed: Mar. 30, 2007

(65) Prior Publication Data

US 2008/0183042 A1    Jul. 31, 2008

(30) Foreign Application Priority Data

Mar. 31, 2006    (EP)    .................................. 06006841

(51) Int. Cl.
G02B 3/06       (2006.01)
G02B 27/02      (2006.01)
A61B 1/00       (2006.01)
A61B 1/06       (2006.01)
G02B 6/32       (2006.01)

(52) U.S. Cl. ....................... 359/710; 359/798; 359/799; 359/800; 359/802; 359/803; 359/809; 359/810; 600/101; 600/139; 600/141; 600/146; 600/160; 600/182; 600/478; 385/32; 385/39; 385/43; 385/51; 385/93; 385/119

(58) Field of Classification Search ................. 600/478, 600/101, 139, 141, 146, 160, 182; 359/710, 359/798–800, 802, 803, 809, 810; 385/32–34, 385/39, 43, 51, 93, 119
See application file for complete search history.

(56) References Cited

U.S. PATENT DOCUMENTS

| 4,148,551 | A | 4/1979 | MacAnally ................... 350/54 |
| 4,813,400 | A * | 3/1989 | Washizuka et al. .......... 600/139 |
| 6,212,015 | B1 | 4/2001 | Heimer ........................ 359/665 |
| 2001/0039371 | A1 | 11/2001 | Forster ........................ 600/176 |

FOREIGN PATENT DOCUMENTS

| EP | 0 587 177 | 3/1994 |
| EP | 1 152 276 | 11/2001 |
| GB | 2099174 A | 12/1982 |
| JP | 62-279309 | 12/1987 |
| WO | WO 95/35522 | 12/1995 |

OTHER PUBLICATIONS

Nusil Silicone Technology "Med. 6010 Product Profile", Sep. 10, 2004, 2 pages.
European Search Report, May 30, 2007, Only considered Document pp. 2-4. Rest of ref. is non-English.
Storz Catalog: The World of Endoscopy - Industrial Endoscopy; 9th Edition; Jan. 2002; 8 pages.

* cited by examiner

*Primary Examiner*—Evelyn A. Lester
(74) *Attorney, Agent, or Firm*—St. Onge Steward Johnston & Reens LLC

(57) ABSTRACT

A rod lens is used for fitting in an endoscopes. The rod lens has a rod-shaped body which is made at least in a section of a flexible, transparent solid piece of plastic material.

18 Claims, 4 Drawing Sheets

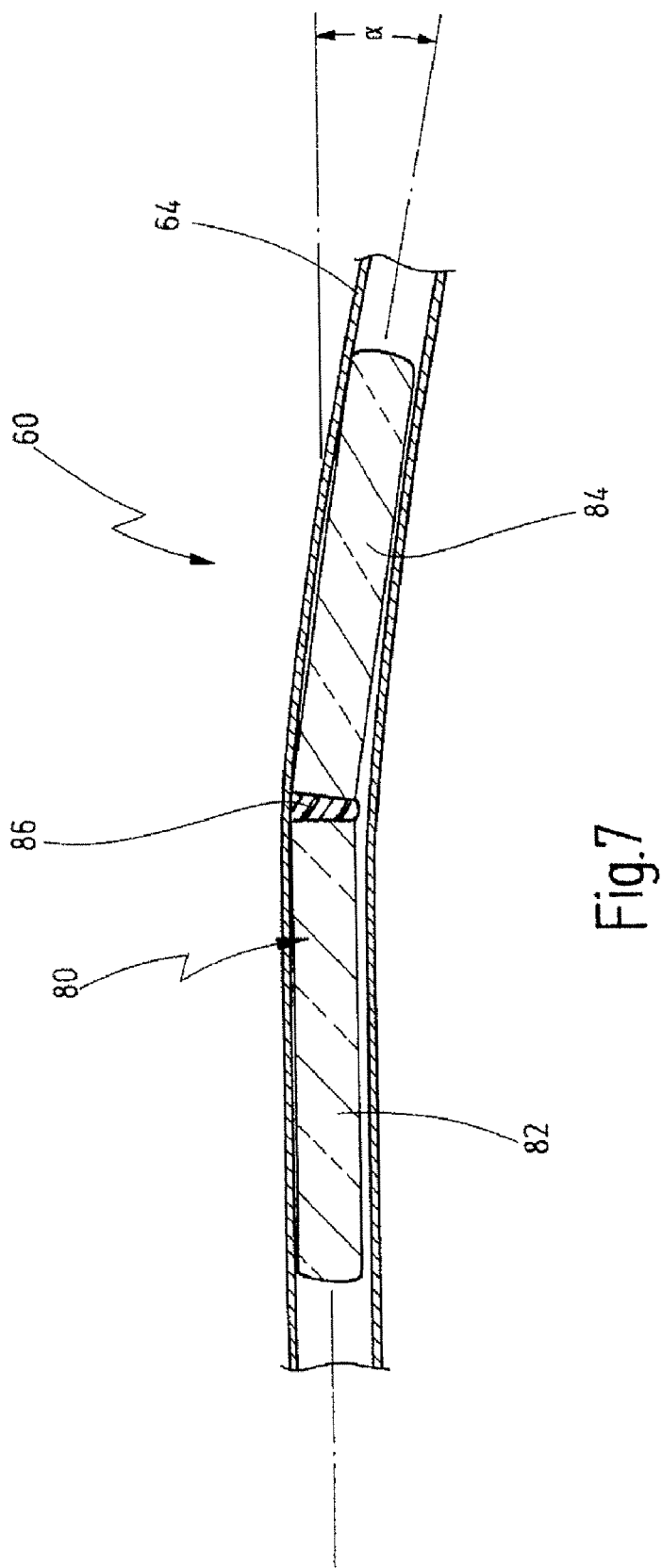

ROD LENS TO BE FITTED IN ENDOSCOPES

BACKGROUND OF THE INVENTION

The present invention relates to a rod lens to be fitted in endoscopes.

Endoscopes of this type have been marketed by Karl Storz GmbH & Co. KG, Tuttlingen, for several decades.

Endoscopes are generally used in minimally invasive surgery for observing body cavities and hollow organs.

Endoscopes have an oblong endoscope shaft in which components of an optical system are arranged. Further devices, usually a light-supply device and conduits for instruments, irrigation liquid for the like, are, moreover, provided inside the shaft. The light is usually supplied via light-guiding glass fibres.

The applicant developed and produced its first endoscope with a traditional lens system in 1953.

The invention of the "Hopkins rod-lens system" (catalogue of Karl Storz GmbH & Co. KG, Tuttlingen, "STORZ, DIE WELT DER ENDOSKOPIE, TECHNISCHE ENDOSKOPIE", $9^{th}$ edition Jan. 2002), which was developed by Karl Storz in cooperation with Professor H. H. Hopkins, was the most crucial breakthrough since the development of the conventional lens system by Nitze in the year 1879.

In Hopkins rod-lens systems, long rod lenses made of glass are used instead of the conventional lenses. These rod lenses have the advantage that they can be used to guide light in an endoscope, for example, with a significantly higher efficiency than is possible using conventional lenses, between which lies a relatively large air space.

The Hopkins rod-lens system thus meets the highest demands of medical diagnostics on account of its excellent image brightness, realistic display and light transfer which is significantly higher compared to the traditional lens system.

At the same time it became possible to crucially reduce the diameter of the endoscope. It was this development, in particular, through which the endoscopes with the Hopkins rod-lens system found wide-spread application in gentle minimally invasive surgery.

The optical system of rigid endoscopes is usually received in a pipe inside the endoscope shaft. Endoscope shafts are very long with respect to their diameter, and conventional diameters are usually in the region of a few millimetres, the length in the region of several decimetres. Accordingly, the diameter of a rod lens is very small with respect to its length, which is several centimetres.

Subjecting the shafts of the endoscopes to bending is inevitable when handling medical endoscopes. Bending of the thin and long endoscope shafts can lead to the relatively long rod lenses made of glass material chipping or even breaking. Damage of this type renders an optical system useless and usually the entire optical system needs to be replaced.

DE 31 13 110 C2 describes giving the rod lenses the shape of a bone in order to produce contact points only at the ends and thereby reduce the risk of breakage.

A further attempt is described in U.S. Pat. No. 4,148,551.

A plurality of rod lenses, which are arranged in the pipe located in the endoscope shaft, are connected to one another by way of a flexible tube. The flexible tube connects two neighbouring rod lenses.

The possibility of bending the endoscope shaft within certain limits without breaking the rod lenses in the process, however, is only partly achieved because of the flexible connection of the rod lenses by using the tube.

If bending moments act directly on the individual rod lens, the rod lens can still break. Such bending moments which act at a point can occur if an endoscope shaft hits an edge, or is dropped, during handling.

It is an object of the invention is to provide a rod lens of the type mentioned in the introduction which can absorb bending moments, in particular bending moments acting at a point, which occur during the use of an endoscope, without the risk of breaking the rod lens.

SUMMARY OF THE INVENTION

The object is achieved according to the invention by a rod lens having a rod-shaped body which is made at least in one section thereof of a flexible, transparent solid piece of plastic material.

This measure has the advantage that making the body in at least one section of a flexible material, the entire rod lens becomes flexible, which strongly reduces the risk of breakage of the rod-lens body. The plastic material is transparent and has optical properties which are very close to those of glass. It has been found that such material can be used to produce rod lenses with high transmissivity and of good optical quality. The provision of a solid piece of flexible, transparent material results in a rod lens which can be handled like a rod lens made of glass only but has a flexibility that is higher in comparison with glass. The flexibility or elasticity of the plastic material is remarkably higher than glass. The hardness of the plastic material is in the range of materials having Shore D hardness values of 80 or less. In particular, the Shore D hardness value is 70 or less, 60 or less or 50 or less. The elongation at tear should be at least 5%. These values depend on the thickness of the material and the desired bending of the rod lens. The smaller the thickness of the piece of plastic material is the softer the material has to be chosen and the greater the elongation at tear is required. Silicone materials are particularly suited for the invention.

Thus the risk of breaking or chipping the rod lens under the usual stresses and strains of a rigid endoscope, to which the endoscope shaft is subjected during handling, for example during the operation or when laying the endoscope down, and also during cleaning, for example through contact with further appliances to be cleaned or during cleaning by ultrasound, is significantly reduced, since the entire rod-lens body is flexible and bendable.

In one refinement, the body of the rod lens has at least two rod elements made of glass, which are assembled by means of a flexible, transparent solid intermediate piece to form the rod-shaped body.

These measures have the significant advantage that such a construction of the rod lens achieves a desired flexibility. The soft and flexible piece allows a bending about it. The flexible piece provides a kind of hinge allowing a bending or buckling of the two glass elements connected via the flexible piece.

This can be illustrated by a conventional rod lens made of glass being split into at least two parts and by these parts being joined together via the flexible, transparent solid intermediate piece to form a rod-lens body.

The flexible intermediate piece ensures that the rod lens is protected against external laterally acting forces, since the connections between the rigid glass rods are very elastic and can therefore dampen impacts. The risk of breaking the glass bodies of the rod lenses is thus significantly reduced even if the endoscope is laid down with some force or even if it is dropped, since bending or even kinking of the rigid glass body about the flexible connecting piece is possible to a certain extent.

The light transfer, the image brightness and the contrast are not impaired by the fact that the flexible intermediate piece provided according to the invention is also transparent.

In a further refinement of the invention, the body is assembled from more than two elements, with two neighbouring elements being connected to one another via an intermediate flexible piece in each case.

This measure has the advantage that the flexibility of the rod lens, which is composed of a plurality of relatively short rod-shaped elements made of glass, increases significantly, with two neighbouring elements being connected to one another via an intermediate flexible piece in each case.

A rod lens of this design has a significantly higher stability with respect to bending moments which act at a point and bending of the endoscope shaft in comparison with the stability of the conventional rod lens, which has the same length.

The risk of breakage of the rod lens is thereby significantly reduced, even if an endoscope is bent very extremely.

In another refinement of the invention, the flexible piece is in the form of highly flexible optical cement.

This measure has the advantage that the cement not only connects the elements such that they adhere to one another, but is non-scattering and does not impair the light transfer, the image brightness and the contrast.

In a further refinement of the invention, the connection sites of the elements are planar or optically active.

These measures have the advantage that in planar interfaces between cement and glass, the beam guidance of the light remains unchanged and it is not necessary to recalculate the existing lenses.

In optically active connection sites, these need to be included in the calculation of optical properties of the entire rod lens.

In a further refinement of the invention, the body is assembled from a piece of glass and a piece of the flexible, transparent solid plastic material.

This measure has the advantage that the rod lens is substantially more flexible in that region in which it is made of the flexible, transparent solid plastic material than in the section which is made of glass. A rod lens of this type can thus have a relatively long section made of the flexible material, for example more than half of its length or more.

Rod lenses of this design can be used at particularly critical regions of the endoscope. One such particularly critical site is for example the transition between the shaft of the endoscope and the housing. Bending or kinking sometimes occurs at this site. If a previously mentioned lens is now used here, it can be fitted such that its highly flexible section comes to bear exactly at this critical site, which significantly lowers the risk of breakage.

In a further refinement of the invention, the body of the rod lens is made entirely of a flexible, transparent solid piece of plastic material.

This measure has the advantage that rod lenses of this type can be used at particularly neuralgic sites in the endoscope shaft at which breaking or chipping of glass lenses has been observed, for example at the abovementioned transition between endoscope housing and endoscope shaft.

In a further refinement of the invention, a lens made of glass is attached at least at one end of the body made of plastic material.

This measure has the advantage that the flexibility of the rod-lens body is essentially determined by the material properties of the plastic material used, but that the optically active end sites can be improved by small glass lens pieces which may possibly be attached.

In a further refinement of the invention, the body has the shape of a bone.

This measure has the advantage that the bone shape as such is already less susceptible to breakage in itself, since only the enlarged "bone ends" of the body are in direct contact with the surrounding tube or shaft housing the rod lens.

If, according to the invention, such a bone-shaped body is replaced at least in sections by, or even completely made of, the flexible plastic material, the flexibility increases significantly further still, with the result that damage to the rod lens can be precluded even for the most massive of shocks.

In one refinement of the invention, one or more rod lenses according to the invention are received in an endoscope, in an optical pipe located inside the shaft.

It is understood that the abovementioned features and those which are still to be explained below can be used not only in the stated combinations but also in other combinations without leaving the scope of the present invention.

BRIEF DESCRIPTION OF THE DRAWINGS

The invention is described and explained in more detail below using a selected exemplary embodiment in conjunction with the drawings, in which:

FIG. 7 shows an enlarged section of the endoscope of FIG. 6 with a bent shaft.

DETAILED DESCRIPTION OF PREFERRED EMBODIMENTS

Figure 1:
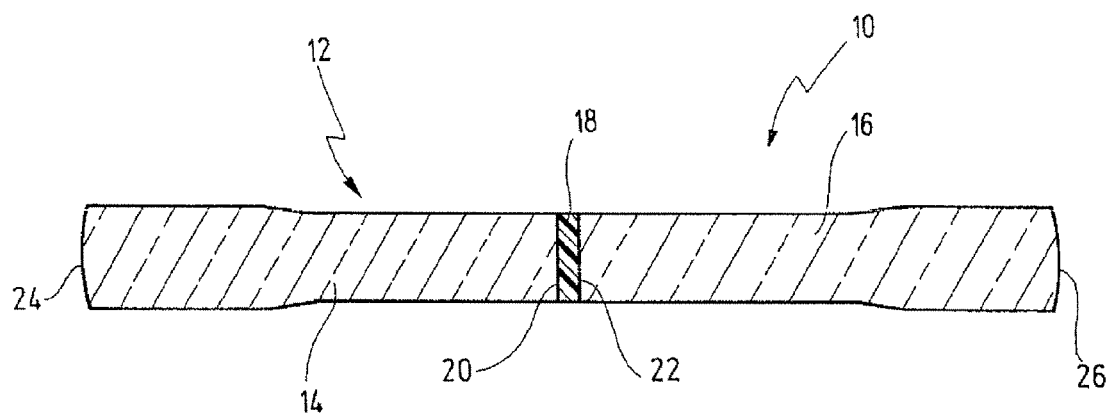
FIG. 1 shows a longitudinal section through a rod lens whose body has the shape of a bone and has two elements made of glass.

The rod lens illustrated in FIG. 1 is denoted in its entirety with the reference numeral 10.

The rod lens 10 has a bone-shaped rod-shaped body 12. A bone-shaped body is one in which there is a rod lens having a cylindrical body, wherein the two opposite end parts have a slightly larger diameter than the part lying between the end parts.

The rod lens 10 has a bone-shaped rod-shaped body 12. A bone-shaped body is one in which there is a rod lens having a cylindrical body, wherein the two opposite end parts have a slightly larger diameter than the part lying between the end parts.

The body 12 is assembled from two mirror-symmetrical elements 14 and 16 which are approximately of the same size, to be more specific via a flexible, transparent solid intermediate piece 18.

The two elements 14 and 16 are made of glass and can be produced by splitting a conventional bone-shaped rod lens 10 in the middle by means of a cross section. This produces two planar opposing connection sites 20 and 22. The elements 14 and 16 are provided, as is customary, at their outer end sides with optically active faces, here with convex faces 24 and 26.

The intermediate piece 18 is made of a curable cement which is flexible even in the cured state. This makes it possible for the elements 14 and 16 connected in FIG. 1 by the intermediate piece 18 to be moved to a certain extent, for example by swinging about the intermediate piece 18. The cured cement has a thermal resistance which withstands the temperatures which occur in the sterilization of an endoscope in an autoclave. The cement further has sufficient strength, expansibility and tensile strength for the connection of the opposing connection sites 20 and 22 to be permanently fixed. Another property of the cement is the transparency. The cement does not scatter light and can be processed bubble-free. The light transfer, the image brightness and the contrast are therefore not impaired by the intermediate piece 18. Cements of this type having the abovementioned properties are available from DELO Industrieklebstoffe GmbH & Co. KG, Landsberg, Germany under the product designation "Katiobond 3019".

Figure 2:
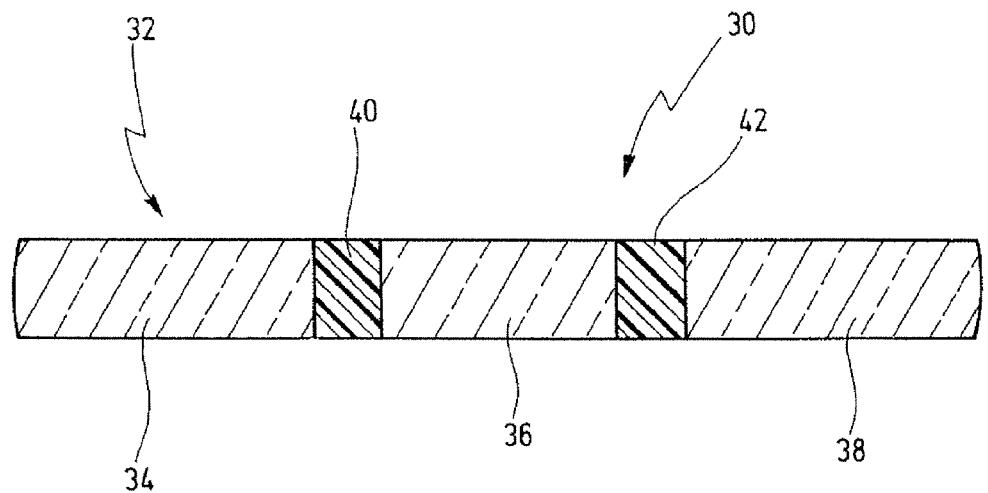
FIG. 2 shows a longitudinal section through a rod lens having three elements made of glass.

In the further exemplary embodiment, illustrated in FIG. 2, a rod lens 30 has a cylindrical body 32. The cylindrical body 32 is assembled from three elements 34, 36 and 38 made of glass, wherein two intermediate pieces 40 and 42 are used for this purpose. The central element 36 is in the form of a cylindrical body with planar end faces or connection sites. This central element 36 is connected to the in each case outer connecting elements 34 and 38 by way of the two connecting pieces 40 and 42, to be more specific by way of planar connection sites.

The in each case outer end face of the elements 34 and 38 is of convex design.

The intermediate pieces 40 and 42 are likewise produced from the abovementioned cement. Providing two flexible sites results in an ever higher flexibility or resistive force with respect to bending stresses and shear loads. A plurality of connection sites are used if the rod lens is extremely long.

Figure 3:
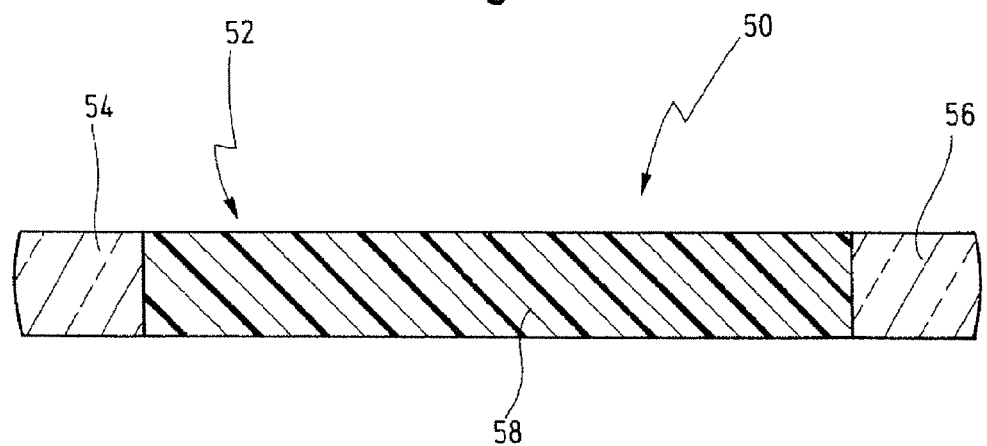
FIG. 3 shows a longitudinal section through a rod lens, in which the piece of cement is very long with respect to the elements made of glass.

In the exemplary embodiment illustrated in FIG. 3, the rod lens 50 likewise has an oblong cylindrical body 52, which is assembled from two elements 54 and 56 made of glass which are connected to one another via an intermediate piece 58.

Here, too, the intermediated piece 58 is again made of the abovementioned material.

In comparison with the exemplary embodiment of FIG. 1, it can be seen that the length of the intermediate piece 58 is very large with respect to the length of the elements 54 and 56 made of glass.

It is possible, on account of the abovedescribed material properties, to produce the intermediate piece such that it is relatively long. This produces a body 52 which can be bent in the region of the intermediate piece 58 to a significant extent. Planar connection sites exist here too between the elements 54 and 56 and the intermediate piece 58. The outer end faces of the elements 54 and 56 are convex.

The material the intermediate piece 18 of the FIG. 1 embodiment is chosen to be very flexible, for example with a Shore D value of less than 50.

The material of the intermediate piece 58 is chosen less softer and may have a Shore D value in the range of 60 to 70. Again, the chosen value depends on the degree or extend of desired flexibility.

Figure 4:
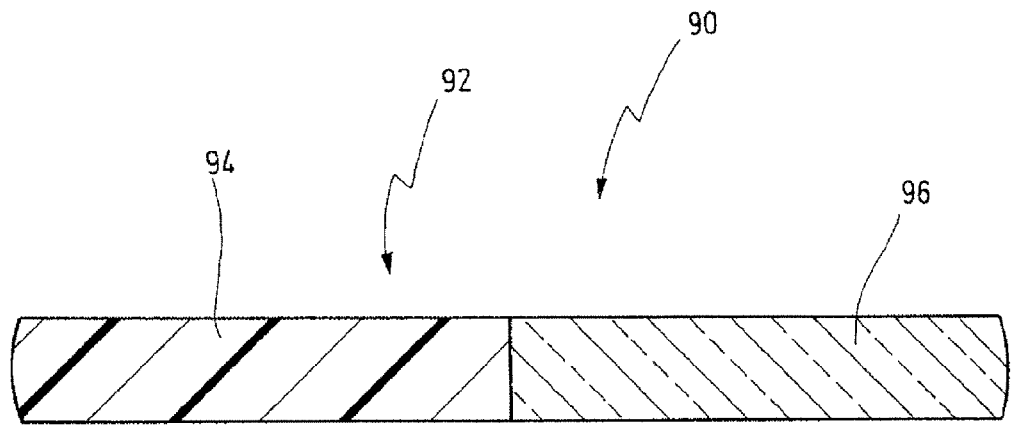
FIG. 4 shows a longitudinal section through a rod lens which is assembled from an element made of glass and a piece made of the flexible plastic material.

FIG. 4 illustrates another exemplary embodiment of a rod lens 90. The body 92 is made of, for example, two pieces 94 and 96 of equal length. The piece 94 is produced from the abovementioned plastic material, the piece 96 is composed of glass. This design gives the body 92 a particularly high flexibility in the region of the piece 94.

Figure 5:
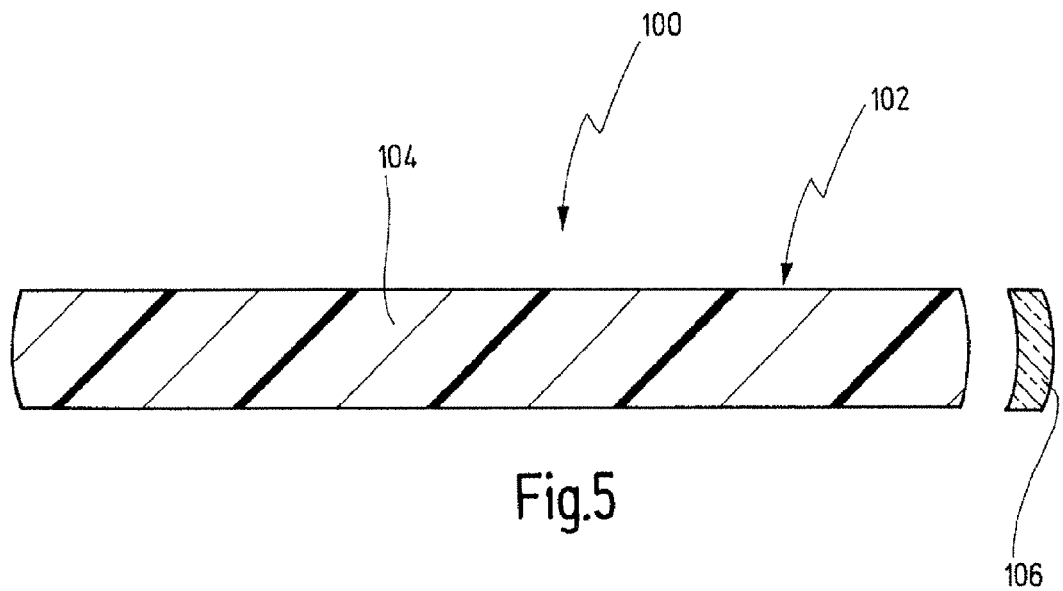
FIG. 5 shows a longitudinal section through a rod lens which is produced entirely from the flexible plastic material.

FIG. 5 illustrates a further exemplary embodiment of a rod lens 100 whose body 102 is produced entirely from a piece 104 of the abovementioned plastic material. The rod lens 100 is used at particularly critical regions, i.e. regions which are susceptible to bending or the action of forces, of an endoscope. If necessary, a thin lens 106 made of glass material can also be attached at the ends to improve the optical properties.

Figure 6:
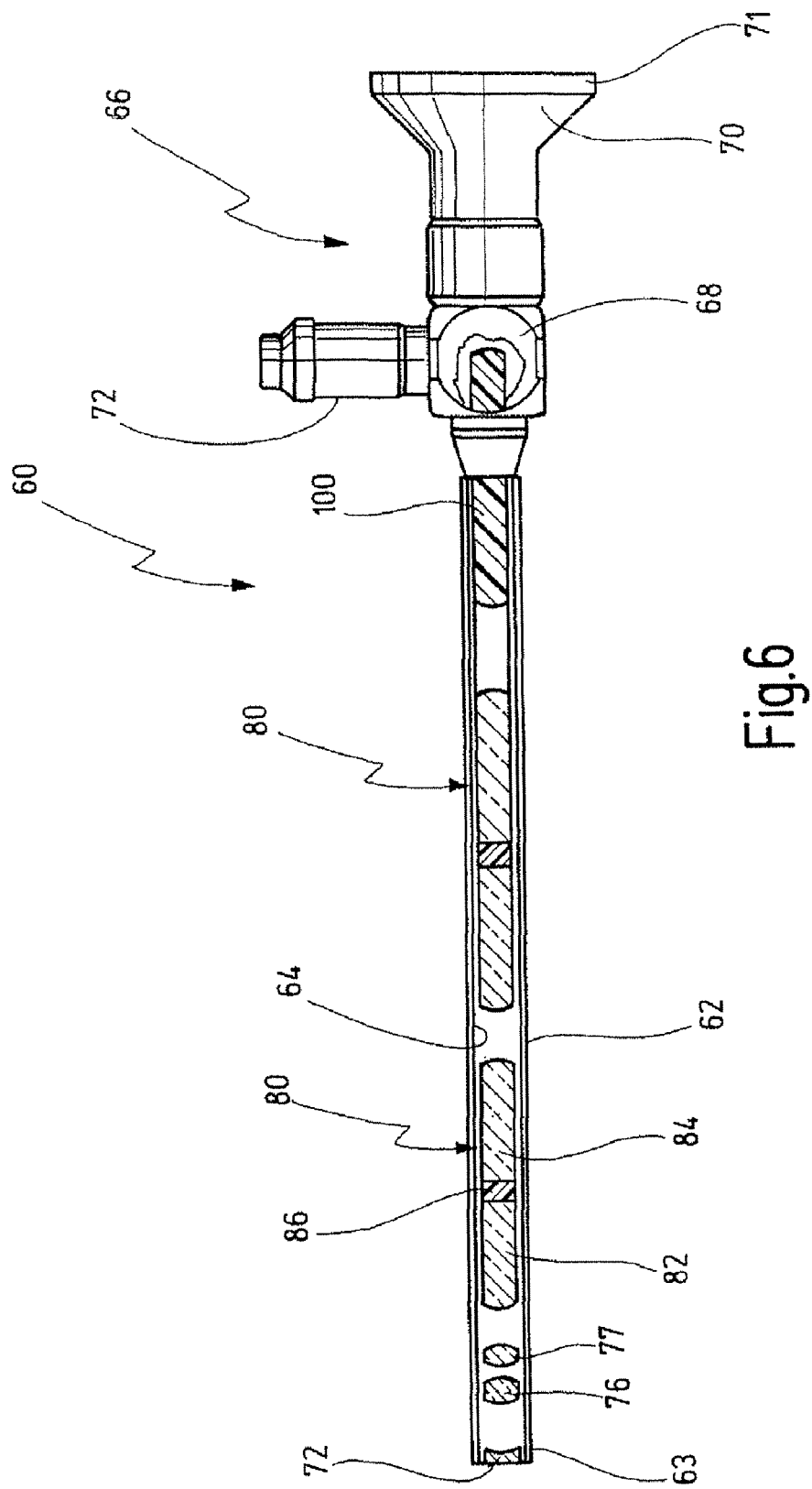
FIG. 6 shows a partially sectioned side view of an endoscope having rod lenses according to the invention.

FIG. 6 illustrates an endoscope 60.

The endoscope 60 has a shaft 62 in which an inner optical pipe 64 is received which is used to receive an optical system. The shaft 62 is connected to a head 66, having a housing 68, an end-side eyepiece 70 and a laterally projecting light guide connection 72, as is customary in endoscope construction.

At the end-side, the shaft 62 is terminated by a window 72, and lenses 76 and 77 form a distal end section of the optical system.

Two rod lenses 80 and the rod lens 90 illustrated in FIG. 5 are received in the optical pipe 64. The rod lenses 80 are constructed from two elements 82 and 84 made of glass, which are assembled via an intermediate piece 86. The highly flexible lens 100 lies in the critical transition region from endoscope shaft 62 to the housing 68.

It can be clearly seen in the side view of FIG. 6 that components project from the head 66 of the endoscope 60 which extend far beyond the outer diameter of the shaft 62.

If, for example, the endoscope 60 illustrated in FIG. 6 falls in this orientation onto the ground, first the outer edge 71 of the eyepiece 70 hits the ground. As a result, the endoscope 60 tilts somewhat and the shaft 62 will then strike the ground with its distal end 63.

Significant bending moments act on the shaft 62 in the process and bend the shaft 62. These forces tend, in particular, to cause the shaft 62 to swing about the connection site with the housing 68. The increased flexibility of the received rod lenses 80 and 100 strongly reduces breaking of the rod lenses. This contributes to a significant increase in the lifespan of the endoscope 60.

FIG. 7 shows the shaft and the optical pipe 64 receiving the optical system being bent in the area of the rod lens 80 about an angle α out of the longitudinal axis. A usual rod lens made of glass having the same length as the rod lens 80 will be fractured at such an extend of bending.

Due to the flexibility or elasticity of the intermediate piece 86 such a bending is possible without the risk of breakage.

The connection sites between the glassy bodies and optical cement were each described as planar connection sites.

This will be the case, as mentioned above, mainly if rod lenses known per se in terms of their optical properties are connected to one another by a cement layer in order to increase the flexibility.

If completely new rod lenses are constructed, it is also possible to design the connection sites as optically active faces, for example convex or concave.

What is claimed is:

1. A glass rod lens to be fitted in an endoscope, said rod glass lens having a longitudinally extending rod-shaped body, wherein said body has at least two stiff rod-shaped glass elements, which are assembled via a flexible, transparent solid intermediate piece, said intermediate piece having a flexibility which is greater than a flexibility of said at least two stiff glass elements, said intermediate piece allowing to bend two neighbored stiff glass elements about an angle α out of a longitudinal axis of said rod-shaped body, said intermediate piece acts as a hinge during a bending movement of said at least two stiff glass pieces, and wherein said flexible, transparent solid intermediate piece is cured cement connecting said at least two stiff glass elements.

2. The rod lens of claim 1, wherein connection sites of said at least two elements are planar.

3. The rod lens of claim 1, wherein connecting sites of said elements are optically active.

4. The rod lens of claim 1, wherein a lens made of glass is attached to at least one end of said body.

5. The rod lens of claim 1, wherein said rod-shaped body has a shape of a bone.

6. The rod lens of claim 1, wherein said cement material has a Shore D hardness value of less than 80.

7. The rod lens of claim 1, wherein said cement material has a Shore D hardness value of less than 70.

8. The rod lens of claim 1, wherein said cement material has a Shore D hardness value of less than 60.

9. The rod lens of claim 1, wherein said cement material has a Shore D hardness value of less than 50.

10. An endoscope having an optical pipe receiving one or more rod glass lenses, said rod glass lens having a longitudinally extending rod-shaped body, wherein said body has at least two stiff rod-shaped glass elements, which are assembled via a flexible, transparent solid intermediate piece, said intermediate piece having a flexibility which is greater than a flexibility of said at least two stiff glass elements, said intermediate piece allowing to bend two neighbored stiff glass elements about an angle a out of a longitudinal axis of said rod-shaped body, said intermediate piece acts as a hinge during a bending movement of said at least two stiff glass pieces, and wherein said flexible, transparent solid intermediate piece is cured cement connecting said at least two stiff glass elements.

11. The endoscope of claim 10, wherein connection sites of said at least two elements are planar.

12. The endoscope of claim 10, wherein connecting sites of said elements are optically active.

13. The endoscope of claim 10, wherein a lens made of glass is attached to at least one end of said body of cement material.

14. The endoscope claim 10, wherein said rod-shaped body has a shape of a bone.

15. The endoscope of claim 10, wherein said cement material has a Shore D hardness value of less than 80.

16. The endoscope of claim 10, wherein said cement material has a Shore D hardness value of less than 70.

17. The endoscope of claim 10, wherein said cement material has a Shore D hardness value of less than 60.

18. The endoscope of claim 10, wherein said cement material has a Shore D hardness value of less than 50.

* * * * *